United States Patent [19]

Heinze

[11] Patent Number: 5,043,707

[45] Date of Patent: Aug. 27, 1991

[54] LEVEL INDICATOR FOR LIQUID RESERVOIRS

[76] Inventor: Werner Heinze, Kälberweide 1, D-8911 Finning, Fed. Rep. of Germany

[21] Appl. No.: 395,908

[22] Filed: Aug. 18, 1989

[30] Foreign Application Priority Data

Aug. 22, 1988 [DE] Fed. Rep. of Germany ....... 3828441

[51] Int. Cl.⁵ .............................................. G08B 21/00
[52] U.S. Cl. .................................... 340/618; 324/639; 73/290 R; 128/DIG. 13
[58] Field of Search ........................ 340/620, 621, 618; 128/DIG. 13; 324/637, 639; 342/124; 73/290 R; 604/246

[56] References Cited

U.S. PATENT DOCUMENTS

| | | | |
|---|---|---|---|
| 3,588,859 | 6/1971 | Petree | 340/620 |
| 3,939,360 | 2/1976 | Jackson | 340/620 |
| 4,002,996 | 1/1977 | Klebanoff et al. | 340/620 |
| 4,423,628 | 1/1984 | Richter | 73/304 C |
| 4,589,281 | 5/1986 | Aldrich | 73/290 R |
| 4,598,733 | 7/1986 | Kanno et al. | 128/DIG. 13 |
| 4,749,988 | 6/1988 | Berman et al. | 340/620 |
| 4,833,918 | 5/1989 | Jean et al. | 73/290 R |

FOREIGN PATENT DOCUMENTS

| | | |
|---|---|---|
| 0042186 | 12/1981 | European Pat. Off. . |
| 1908750 | 8/1970 | Fed. Rep. of Germany . |
| 28278032 | 8/1979 | Fed. Rep. of Germany . |
| 3044353 | 6/1982 | Fed. Rep. of Germany . |
| 3421176 | 12/1985 | Fed. Rep. of Germany . |

Primary Examiner—Joseph A. Orsino
Assistant Examiner—Jill Jackson
Attorney, Agent, or Firm—Price, Heneveld, Cooper, DeWitt & Litton

[57] ABSTRACT

A level indicator for blood reservoirs, in particular of medical apparatus, having a level-responsive component to be provided on the wall of the blood reservoir is provided with an oscillator set to an operating frequency of greater than or equal to 50 MHz and having integrated into its circuit the level-responsive component which, when a preset limiting value is passed, changes the phase condition or amplitude condition decisive for the oscillation of the oscillator.

30 Claims, 2 Drawing Sheets

LEVEL INDICATOR FOR LIQUID RESERVOIRS

The present invention relates to a level indicator for liquid reservoirs and in particular for use with liquid reservoirs in medical applications, such as for holding blood.

During cardiosurgical operations, for example, it is absolutely necessary to prevent air instead of blood from being pumped into the patient out of the blood reservoir, because even small amounts of air suffice to bring about a fatal air embolism. A reduced venous flow out of the patient, for instance, can lead to a rapid drop in the blood reservoir level of an oxygenator, so that the liquid level must be constantly monitored during the operation.

It is already known to read a drop below a minimum level via the weight, but the scales must be absolutely insensitive to all external influences which might alter the weight, such as a change of position in the tubes, blows against the oxygenator and the like. In practice, such a measuring method results in an extremely elaborate mechanical device which is not particularly reliable.

Finally, optical measuring methods are known which make use of the fact that blood absorbs light due to its dark color, so that when blood is present the angles of refraction on the boundary surfaces vary. The disadvantage of these optical methods, however, is that different mechanical sensor attachments are required for different blood reservoirs. With some types of oxygenators, the optical method can only be used when blood is already in the oxygenator, while clear liquids are taken to be air.

Recent developments work on the ultrasound principle. An ultrasound sensor provided on the wall of the blood reservoir, after appropriate electrical excitation, imitates a sound wave through the walling of the oxygenator into the interior thereof. The frequency of the ultrasound wave is in the range of about 2 MHz. If there is liquid in the oxygenator, the wave can expand. If it hits a boundary surface, part of the wave is reflected and runs back to the sound transducer, which is now connected as a receiver. However, since the amplitude of the sound wave is greatly weakened on its way through the blood reservoir, very sensitive amplifiers are required, so that the ultrasound methods are very interference-prone. A further disadvantage is that the ultrasound methods are only applicable for certain types of plastics, in particular macrolon, and not for other materials. Furthermore, interference factors can result from the wall thickness, since thick walls lead to wall reflections, which brings about uncertain states. A further disadvantage is that an ultrasound gel for transmitting energy to the wall of the blood reservoir must be used to couple the sensor.

The invention is based on the problem of providing a level indicator for liquid reservoirs, in particular for blood reservoirs of apparatus for human medicine, which is largely free from interference and thus ensures reliable operation, and is also easy and inexpensive to produce.

This problem is solved according to the invention by the features contained in the characterizing part of claim 1, expedient developments of the invention being characterized by the features contained in the subclaims.

According to the invention, the level indicator has an oscillator set to an operating frequency of greater than or equal to 50 MHz and having disposed in its circuit the level-responsive component which, when a preset limiting value is passed, changes the phase condition or amplitude condition determining the oscillation of the oscillator.

The invention utilizes the fact that an oscillator comprising basically a feedback network and amplifier is capable of oscillating when two conditions are met, namely $$kv = 1 \quad (1)$$

$$\alpha + \beta = n\pi \quad (2)$$

wherein n signifies an integer.

v signifies the factor by which the amplifier amplifies input voltage Ue of the oscillator. The angle $\alpha$ is the value of phase difference of output voltage Ua, which is greater than input voltage Ue by factor v. The feedback network of the oscillator receives as its input voltage the output voltage of the amplifier, reduces the input voltage by factor k and shifts the phase of the signal by angle $\beta$.

Equation (1) is referred to as the amplitude condition. An oscillator oscillates only when the value of the amplitude condition is greater than or equal to 1. Equation (2) is referred to as the phase condition and says that oscillation comes about only when the output voltage of the feedback network is in phase with the input voltage of the amplifier. According to the invention, a component is added at any point in the oscillator circuit that changes its value in accordance with the level in such a way that either the phase condition or the amplitude condition is no longer given so that one obtains a formation that oscillates or not depending on the level.

In an expedient embodiment, this level-responsive component is embodied by a dipole which is preferably disposed at the output of the feedback network, and is also adjusted to the oscillating frequency of the oscillator. If the level is above the dipole, the latter can radiate energy into the liquid, thereby reducing the output voltage of the feedback network so that the amplitude condition is no longer met. The product kv is smaller than 1, so that the oscillator no longer oscillates when the level is above the safety level monitored by the dipole. As soon as the liquid level has dropped below the level of the dipole, the amplitude condition is met and the oscillator oscillates, which can be made perceptible in a suitable way, in particular acoustically or optically, so that the level can be suitably regulated. The invention is particularly suitable for blood reservoirs in containers made of plastics or glass (not lead glass). It is also suitable for other liquids based on water, such as nutrient solutions, urine and the like, in particular wherever one is not supposed to come in contact with the content of the container.

As an alternative to the dipole, one can use a capacitor which is expediently built into the feedback network of the oscillator circuit in such a way that it is decisive for the phase relation of the output signal. If it is also dimensioned such that the oscillating condition is only met when the level is higher than the liquid level caused by the position of the capacitor, a drop in the level below the liquid level caused by the capacitor causes a change in the phase condition, so that the addition of the phase differences $\alpha$ and $\beta$ is not equal to an integral multiple of $\pi$, so that when the limiting value determined by the position of the capacitor is passed the oscillator no longer oscillates and the level must thus be regulated.

The dipole or the capacitor is expediently insulated from the outside environment to eliminate influences due to condensation water and the like. The insulation is expediently provided by plastics material. A suitable material for the carrier is any that can take up the dipole or capacitor and allow for it to be mounted on the wall of the blood reservoir. The carrier must be flexible. It is expedient to use a material for printed circuits, so that the oscillator can be integrated into the carrier material, i.e. in particular formed by a printed circuit. According to an alternative, the oscillator is of removable design and can be plugged onto plug contacts formed on the dipole or capacitor.

The operating frequency expediently has a value greater than or equal to 100 MHz and is in particular in the microwave range, which is advantageous for the dimensioning of the dipole or capacitor.

All in all, the invention level indicator is characterized by the fact that it can be used for all plastics, but also for other materials such as in particular, glass and ceramics. Furthermore, the level indicator is very easy to produce, so that it is suitable in particular as a disposable product. The inventive level indicator is particularly characterized by its freedom from interference, thereby allowing for very exact and reliable level measurement. By selecting the operating frequency range, one can eliminate any influences due to interfering frequencies which may result from other apparatus being used in the opening theater area.

In the following, exemplary embodiments of the invention shall be described with reference to the drawing, in which FIG. 1 shows a schematic perspective view of a level indicator on a container-like blood reservoir;

Figure 1:
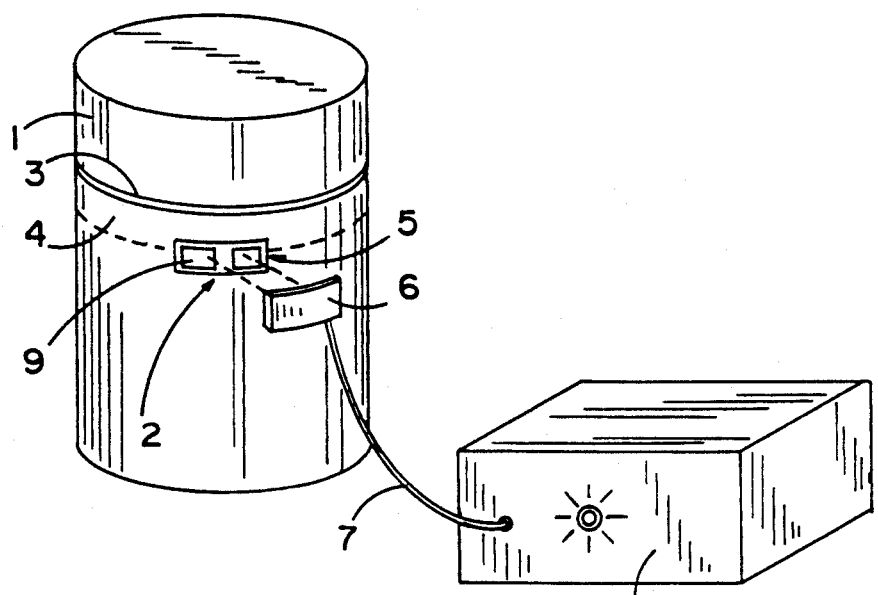

In FIG. 1, reference number 1 refers to a container serving as a blood reservoir which can be used, for example, in conjunction with an oxygenator or similar medical apparatus. In such a container it is necessary to maintain a certain level of blood, for example. This is obtained using the level indicator referred to in general as 2 in FIG. 1, that is disposed at the height of the desired liquid level. The liquid level currently prevailing in the container is referred to as 3. The desired level is marked schematically by a broken line and referred to as 4.

Level indicator 2 shown in FIG. 1 contains a dipole 5 to which an oscillator 6 can be connected. Oscillator 6 is connected via a line 7 with a suitable evaluating device 8.

Figure 2:
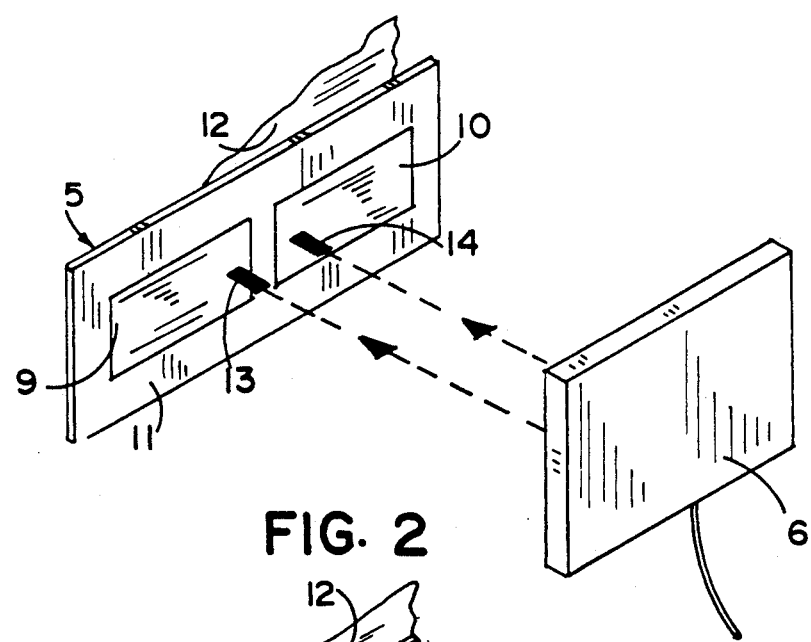
FIG. 2 shows a view of an embodiment of the level indicator.

FIG. 2 shows the level indicator equipped with a dipole in greater clarity. Two metal surfaces 9 and 10, which form dipole 5, are disposed side by side on a carrier referred to as 11 for mounting the dipole on the wall of container 1. In the embodiment shown, the carrier is coated on the side facing the wall of the container with an adhesive which is protectively covered from the outside by a removable foil 12. On metal surfaces 9 and 10 forming the dipole there are plug contacts 13 and 14 onto which oscillator 6 can be plugged.

Figure 3:
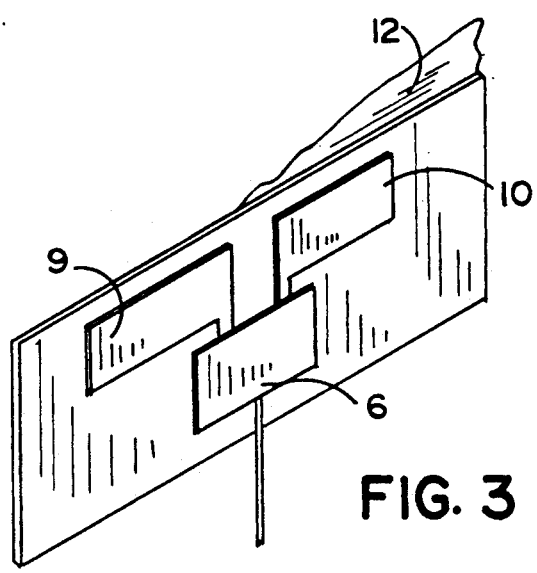
FIG. 3 shows a schematic view of another embodiment of the level indicator.

In the embodiment of FIG. 3, the oscillator is connected firmly, i.e. latently, with the metal surfaces forming the dipole, being in particular potted with the metal surfaces under the carrier material. In a special embodiment, carrier 11 is made of a material for printed circuits, so that the oscillator may be printed onto the carrier. Dipole 5 is expediently insulated from the outer environment by casting round the dipole that, like the carrier, is of flexible design, with plastics. This measure prevents any disturbance of operation due to condensation water or the like.

The dipole is adjusted to the oscillating frequency of the oscillator. If the level is above the line referred to as 4, i.e. above the dipole, the latter can radiate energy into the liquid, so that a consumption of power takes place. This reduces the output voltage at the back coupler of the oscillator, and the amplitude condition of $kv=1$, that is decisive for the oscillation of the oscillator, is not met so that the oscillator does not oscillate. When the limiting value referred to as 4 is passed, there is no more reduction of the output voltage of the feedback network because the dipole can no longer radiate energy into the liquid. The amplitude condition is therefore now met, so that the oscillator oscillates. This can be made perceptible acoustically or optically, so that the level can be regulated accordingly. Obviously, the dipole is integrated into the oscillator circuit, being expediently disposed at the output of the feedback network of the oscillator.

Figure 4:
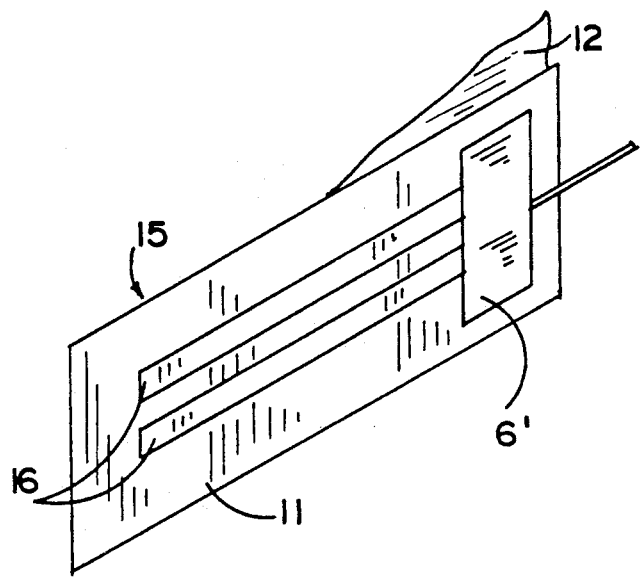
FIG. 4 shows a schematic view of another embodiment of the level indicator.

In FIG. 4 a capacitor is used instead of a dipole as the level-responsive component and is integrated into the oscillator circuit in such a way that the capacitor is decisive for the phase relation of the output signal of the oscillator. Capacitor 15 includes a pair of plates 16 on carrier 11 which are dimensioned such that the oscillating condition is only met when the level in the container is higher than the limiting value referred to as 4, a drop in the level below the value referred to as 4 causes a change in the value decisive for the oscillating condition, i.e. the phase condition, so that the oscillator begins to oscillate when the level is lower than the limiting value referred to as 4. This can also be made perceptible in a suitable way, in particular optically or acoustically, so that the level can be regulated accordingly.

Figure 5:
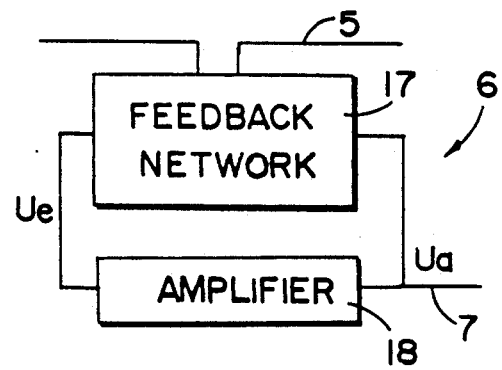
FIG. 5 shows a block diagram of the embodiment of the level indicator in FIG. 2.
Figure 6:
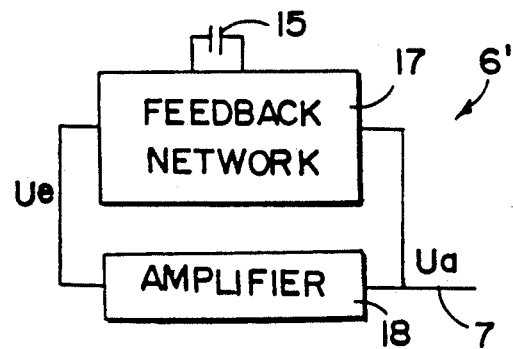
FIG. 6 shows a block diagram of the level indicator in FIG. 4.

Oscillator 6 is shown in FIG. 5 having a feedback network 17 connected with the output Ua of an amplifier 18. Feedback network 17 has an output connected with input Ue of amplifier 18. Dipole 5 is connected with feedback network 17. In FIG. 6, capacitor 15 is shown connected with feedback network 17' of oscillator 6'.

The operating frequency of the oscillator is greater than or equal to 50 MHz, in particular greater than or equal to 100 MHz, and is preferably in the microwave range. The microwave range is suitable because it allows for the level-responsive component to be of small dimensions. The latter can then be approximately the size of an adhesive plaster and thus be very easily attached to a container wall by means of a suitable carrier.

The embodiments of the invention in which an exclusive property or privilege is claimed are as follows:

1. A level indicator for a liquid reservoir having liquid-retaining walling defining said reservoir and used in a medical apparatus, comprising:
a level responsive component which comprises a dipole including a carrier having means for mounting said dipole on an external surface of said liquid reservoir walling, an oscillator set to an operating frequency at least as high as 50 MHz and including said dipole integrated therein, and wherein said dipole is adjusted to said oscillating frequency and responsive to a preset limiting value and adapted to change one of a phase condition and an amplitude condition decisive for oscillation of said oscillator in response to said preset limiting value being passed.

2. The indicator of claim 1, wherein said dipole is insulated from the outside environment.

3. The indicator of claim 1, wherein said dipole is disposed at the height of the reservoir liquid level corresponding to said limiting value.

4. The indicator of claim 1, wherein said dipole is made of metal.

5. The indicator of claim 4, wherein the operating frequency of said oscillator is at least as high as 100 MHz.

6. The indicator of claim 5, wherein the operating frequency of said oscillator is in the microwave range.

7. The indicator of claim 1, wherein said dipole has plug contacts, and said oscillator is adapted to be plugged on said dipole plug contacts.

8. The indicator of claim 7, wherein the operating frequency of said oscillator is at least as high as 100 MHz.

9. The indicator of claim 8, wherein the operating frequency of said oscillator is in the microwave range.

10. The indicator of claim 1, wherein said dipole is disposed on a flexible carrier attached to said walling of a blood reservoir.

11. The indicator of claim 10, wherein said flexible carrier is self-adhesive.

12. The indicator of claim 10, wherein said flexible carrier is made of a material used for printed circuits, and said oscillator is integrated into said flexible carrier material.

13. The indicator of claim 10, wherein said dipole has plug contacts, said oscillator is adapted to be plugged on said dipole plug contacts.

14. The indicator of claim 10, wherein said dipole is disposed at the height of the reservoir liquid level corresponding to said limiting value.

15. The indicator of claim 1, wherein the operating frequency of said oscillator is at least as high as 100 MHz.

16. The indicator of claim 15, wherein the operating frequency of said oscillator is in the microwave range.

17. The indicator of claim 16, wherein said dipole is disposed at the height of the reservoir liquid level corresponding to said limiting value.

18. The indicator of claim 15, wherein said dipole is disposed at the height of the reservoir liquid level corresponding to said limiting value.

19. The indicator of claim 1, wherein said oscillator has a feedback network with an output, said dipole being disposed at said output of said feedback network of said oscillator.

20. The indicator of claim 19, wherein said dipole is insulated from the outside environment.

21. The indicator of claim 19, wherein said dipole has plug contacts, said oscillator is adapted to be plugged on said dipole plug contacts.

22. The indicator of claim 19, wherein said dipole is disposed at the height of the reservoir liquid level corresponding to said limiting value.

23. The indicator of claim 19, wherein said dipole is made of metal.

24. The indicator of claim 23 wherein said dipole is insulated from the outside environment.

25. The indicator of claim 19, wherein the operating frequency of said oscillator is at least as high as 100 MHz.

26. The indicator of claim 25, wherein the operating range of said oscillator is in the microwave range.

27. The indicator of claim 19, wherein said dipole is disposed on a flexible carrier attached to said walling of said blood reservoir.

28. The indicator of claim 27, wherein said flexible carrier is self-adhesive.

29. The indicator of claim 27, wherein said flexible carrier is made of a material used for printed circuits, and said oscillator is integrated into said flexible carrier material.

30. The indicator of claim 27, wherein said dipole has plug contacts, said oscillator is adapted to be plugged on said dipole contacts.

* * * * *

UNITED STATES PATENT AND TRADEMARK OFFICE
CERTIFICATE OF CORRECTION

PATENT NO. : 5,043,707

DATED : August 27, 1991

INVENTOR(S) : Werner Heinze

It is certified that error appears in the above-identified patent and that said Letters Patent is hereby corrected as shown below:

Column 3, line 33:

"opening" should be --operating--.

Signed and Sealed this

Twentieth Day of April, 1993

Attest:

MICHAEL K. KIRK

Attesting Officer

Acting Commissioner of Patents and Trademarks